US00PP36730P2

(12) United States Plant Patent
Espín

(10) Patent No.: US PP36,730 P2
(45) Date of Patent: Jun. 10, 2025

(54) GRAPEVINE PLANT NAMED 'BLOMG03'

(50) Latin Name: *Vitis vinifera*
Varietal Denomination: BLOMG03

(71) Applicant: BLOOM FRESH INTERNATIONAL LIMITED, London (GB)

(72) Inventor: Juan Carreño Espín, Murcia (ES)

(73) Assignee: BLOOM FRESH INTERNATIONAL LIMITED, London (GB)

( * ) Notice: Subject to any disclaimer, the term of this patent is extended or adjusted under 35 U.S.C. 154(b) by 0 days.

(21) Appl. No.: 19/019,856

(22) Filed: Jan. 14, 2025

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./156, 205
See application file for complete search history.

(56) References Cited

U.S. PATENT DOCUMENTS

| | | | | |
|---|---|---|---|---|
| PP3,106 | P | 4/1972 | Garabedian | |
| PP12,696 | P2 * | 6/2002 | Karniel | A01H 5/08 Plt./207 |
| PP33,448 | P2 | 9/2021 | Martinez | |

* cited by examiner

*Primary Examiner* — Karen M Redden
(74) *Attorney, Agent, or Firm* — Michael Best & Friedrich LLP

(57) ABSTRACT

'BLOMG03' is a new and distinct grapevine plant with novel characteristics that include good fertility, naturally loose bunches and is tolerance to *Erysiphe necator*, which is one of the main diseases of this species. The berries produced by 'BLOMG03' are white and seedless with a crunchy texture and muscat flavor and no detectable seed traces. The berries produced by 'BLOMG03' are medium, weighing 5.3 g/berry on average, and harvested in early July in Murcia Region (Spain).

1 Drawing Sheet

Latin name of the genus and species: *Vitis vinifera*.
Variety denomination: 'BLOMG03'.

BACKGROUND

Described herein is a new distinct variety of seedless grapevine named 'BLOMG03' with tolerance to *Erysiphe necator*, one of the main diseases of this species.

The new variety originated from a hybridization performed in Murcia, Spain during 2017 between '12-3-73' ('Itumfifteen' U.S. Plant Pat. No. 33,448), as the pollen parent, and 'RS12-1-158' (not patented), as the seed parent. Abortive seed traces were embryo cultured and the resulting plant was planted in an evaluation block during 2018. The first evaluation of the fruit produced by 'BLOMG03' was performed during 2019. 'BLOMG03' was first asexually propagated by field grafting dormant hardwood scions to 1103 Paulsen Rootstock (not patented) in 2020 in Murcia, Spain. Fruit from the resulting four grafted 'BLOMG03' vines was first harvested in 2021. All characteristics and distinctions remain true to form and are established and transmitted through succeeding propagations.

SUMMARY

The following are the most outstanding and distinguishing characteristics of 'BLOMG03'. 'BLOMG03' produces naturally medium (5.3 g/berry) seedless white (2.5 GY6/6) berries with tolerance to *Erysiphe necator*. The berries produced by 'BLOMG03' have a globose shape with an excellent muscat flavor and crunchy texture, that are harvested in early July in Murcia-Spain.

'BLOMG03' is believed to be most similar to 'Sugraone' (U.S. Plant Pat. No. 3,106). Nonetheless, the new cultivar can be distinguished from 'Sugraone' based at least upon fertility, cluster size, berry shape, and berry flavor. 'BLOMG03' has a fertility index of 1.3 while 'Sugraone' has 0.5 fertility index. The bunches produced by 'BLOMG03' are less heavy (300 g) than the bunches produced by 'Sugraone' (500 g). 'BLOMG03' produces berries with globose shape and muscat flavor while the berries of 'Sugraone' have ovoid shape and neutral flavor.

'BLOMG03' can be distinguished from its male parent, '12-3-73' (U.S. Plant Pat. No. 33,448), in that the new cultivar has a fertility index of 1.1 while 'BLOMG03' has 1.3 fertility index. 'BLOMG03' have clusters less heavy than '12-3-73' clusters (average 300 g vs. 450 g). The berries of 'BLOMG03' are white (2.5 GY6/6) while the berries of '12-3-73' are pink. The berries of 'BLOMG03' have thick skin whereas the berries of '12-3-73' have thin skin.

'BLOMG03' can be distinguished from its female parent, 'RS12-1-158' (not patented), in that the harvest period of 'BLOMG03' is in early July while the harvest period of 'RS12-1-158' is in the end of July (2 weeks later). The berries of 'BLOMG03' are seedless whereas the berries of 'RS12-1-158' are seeded. The bunches of 'BLOMG03' are loose while the bunches of 'RS12-1-158' are compact. The berries of 'BLOMG03' have a crunchy texture whereas the berries of 'RS12-1-158' have a juicy texture.

BRIEF DESCRIPTION OF THE DRAWING OR PHOTOGRAPHS

The accompanying color photographs illustrate the overall appearance of the 'BLOMG03' plant showing the colors as true as it is reasonably possible to obtain in colored reproductions of this type. Colors in the photographs may differ slightly from the color values cited in the detailed botanical description that accurately describe the colors of the plant described herein. These figures are exemplary will vary depending on the plant and distinguishing characteristics.

FIG. 1 shows the form, foliage, and fruit of a 3-year-old 'BLOMG03' vine grown in the field at Murcia, Spain. The colors shown are as true as can be reasonably obtained by conventional photographic procedures.

DETAILED BOTANICAL DESCRIPTION

The following detailed description sets forth the distinctive characteristics of 'BLOMG03'. The detailed description was obtained between March and November using 3-year-old plants grown in the field in Murcia, Spain. The color references are to the Munsell Plant Tissue Color Book, 2012 Edition by Munsell Color.

Classification:

*Family*.—Vitaceae.

*Botanical*.—*Vitis vinifera*.

*Common name*.—Grapevine.

*Cultivar name*.—'BLOMG03'.

Plant:

*Plant habit and growth*.—Erect.

*Age at maturity*.—3 years old.

*Size* (*at maturity*).—Height — 225 cm. Width — 300 cm.

*Vigor*.—Medium.

*Productivity*.—High (1.3 fertility index), around 25 pounds/plant and 12 t/acre.

*Rootstock*.—Name of rootstock — 1103 Paulsen Rootstock (not patented). Age of rootstock at time of grafting — one year old.

Trunk:

*Size*.—Diameter — 5.4 cm. Height (at measured diameter of 5.4 cm) — 45 cm above the ground.

*Shape*.—Straight and cylindrical.

*Surface texture*.—Rough, straight grained with the outer layer easily removed.

*Bark color*.—Exterior — 7.5YR5/4. Interior — 5YR4/6.

Canes:

*Size*.—Diameter — 10.45 mm. Length — 190 cm.

*Surface texture*.—Mature cane — rough and very fined ribbed, very low density of prostrate hairs. Immature cane — very smooth and finely ribbed, glabrous.

*Form* (*woody shoot cross section form*).—Circular; pith in center with diaphragm at nodes.

*Color*.—Mature — 5 months, 5GY6/8 (anthocyanins — 5R3/4). Immature — 4 weeks, 5GY4/8. Dorsal side of internodes — 5R3/4. Ventral side of internodes — 5R3/4. Dorsal side of nodes — 5GY6/8; anthocyanins — 5R3/4. Ventral side of nodes — 5GY6/8; anthocyanins — 5R3/4.

*Internode length* (*upper mature sun cane*).—18 cm.

*Internode width* (*upper mature sun cane*).—9.65 mm.

*Node width*.—14.80 mm.

Bud:

*Bud description*.—Winter bud — rounded, pointed, color 5YR4/4.Green bud — rounded and pointed, 5GY7/8 (without anthocyanin coloration).

*Time of bud burst*.—24 February.

*Time of bud leaf burst*.—9 March.

Tendrils:

*Form*.—Mostly trifid and thick.

*Size*.—Very large.

*Length*.—32 mm.

*Diameter*.—3.1 mm.

*Texture and distribution of tendril at each node beginning at base*.—Very smooth, discontinuous, 00000000100100110010010 0010 (0 means no tendril at that node and 1 means there is tendril at the node).

*Color*.—Mature — 4 weeks, 2.5GY6/8. Immature — 10 days, 5GY5/6.

*Anthocyanin*.—Mature — 5R3/4. Immature — absent.

Growing tips (young shoot):

*Pubescence*.—Present, low density of prostrate hairs on the shoot tip.

*Color*.—2.5GY5/8.

*Anthocyanin*.—Absent.

*Shape*.—Fully open.

*Apex*.—Triangular.

*Form of tip*.—Fully open.

*Shoot attitude before tying*.—Erect.

Leaves:

*Shape*.—Wedge-shaped.

*Apex*.—Pointed.

*Base*.—Cuneiform.

*Number of lobes*.—5.

*Depth of upper lateral sinuses of mature leaves*.—Shallow.

*Arrangement of lobes of upper lateral sinuses on mature leaves*.—Open.

*Margin*.—Irregular teeth.

*Length of teeth on margin*.—2 to 12 mm.

*Shape of teeth on margin*.—Both sides convex.

*Texture* (*mature leaf*).—Upper surface — smooth, glabrous, without goffering or blistering on upper side of blade. Lower surface — smooth, glabrous.

*Size*.—Immature: Length — 10 days, 6.75 cm. Width — 10 days, 6.1 cm. Mature: Length — 4 weeks, 19.3 cm. Width — 4 weeks, 18 cm. Ratio of length/width of teeth (mature leaf) — medium.

*Color*.—

*Immature leaf*.—Upper surface — 5GY4/8, anthocyanins 2.5YR4/4. Lower surface — 5GY5/6.

*Mature leaf*.—Upper surface — 7.5GY3/4. Lower surface — 5GY5/4.

*Autumn coloration*.—Upper surface — 2.5Y8/8. Lower surface — 2.5Y8/6.

*Venation*.—Pattern — palmate (veins on upper leaf are flat; veins on lower leaf are raised), without anthocyanins coloration. Length of middle vein in mature leaves — 15.5 cm.

*Color*.—Upper surface — 2.5GY6/6. Lower surface — 2.5GY8/8.

*Petiolar sinus*.—Open, V-shaped.

*Petiole*.—Length — 10 cm. Diameter — 3.5 mm. Color — 5GY7/8, anthocyanins 2.5R5/8.

Floral cluster:

*General description and location*.—Mostly in the $4^{th}$ and $5^{th}$ node, 100% with shoulders.

*Quantity of inflorescences per cluster*.—400.

*Size*.—Length — 10.5 cm. Width — 5 cm hanging; 9.75 cm with shoulders spread.

*Peduncle*.—Length — 5.25 cm. Diameter — 4.40 mm.

*Inflorescences*.—Hermaphroditic.

*Stamens*.—5 per flower, straight, 3 mm, diameter 0.61 mm.

*Anthers*.—Small, nondescript.

*Date of bloom*.—Start: 24 April; 50%: 29 April; 100%: 3 May.

*Pollen amount*.—Sparse.

*Calyptra*.—5 segments, complete separation.

*Calyptra color*.—5GY4/6.

Fruit:

*Time of year of commercial harvest and shipment*.—Early season, July 15, in Murcia, Spain.

*Time of beginning of berry ripening*.—Early.

*Keeping quality*.—Excellent, after 30 days of refrigerated storage there are no symptoms of dehydration, the stems and berries are well preserved. The variety keeps its excellent muscat flavor and the crispness.

*Cluster* (*primary bunches*).—General size — small (300 g). Length (without peduncle) — 18 cm. Width — 10.3 cm hanging, 15.5 cm with shoulders spread. Density — lax. Peduncle length — 6.1 cm. Peduncle diameter — 6.6 mm. Peduncle color — 2.5GY 5/6. Number of berries per cluster — 60.

*Berry*.—Size — medium (5.3 g). Diameter — 20.14 mm. Length — 20.70 mm. Shape — globose. Uniformity — very uniform. Brix content — 19.8° Brix. Titratable acidity — 0.56. Skin color (without bloom) — 2.5GY6/6. Skin color (with bloom) — 2.5GY6/6.

*Pedicel*.—Length — 9 mm. Diameter — 1.25 mm. Color — 5GY7/6. Strength of attachment to berry — very strong, 15%.

*Cluster* (*secondary bunches*).—General size — small, 72.5 g. Length (without peduncle) — 7.75 cm. Width — 7 cm hanging; 8.75 cm with shoulders spread. Density — lax. Peduncle length — 6 cm. Peduncle diameter — 3.33 mm. Peduncle color — 2.5GY5/6.

*Number of berries per cluster*.—19 (on average).

*Berry*.—Size — small, 3 g. Diameter — 17.3 mm. Length — 17.2 mm. Shape — globose. Uniformity — very uniform. Brix content — 20.1° Brix. Titratable acidity — 0.58. Skin color (without bloom) — 2.5GY6/6. Skin color (with bloom) — 2.5GY6/6. Pedicel: Length — 7.6 mm. Diameter — 1.6 mm. Color — 5GY7/6. Strength of attachment to berry — very strong, 10%.

Berry flesh:

*Color*.—2.5GY8/4.

*Juice, color*.—2.5Y8/8.

*Juice production*.—High, 38.5%.

*Thickness of skin*.—Thick.

*Flavor*.—Muscat.

*Fragrance*.—Neutral, herbaceous.

*Texture*.—Crunchy, 70 shores.

*Seeds*.—Seed rudiments, non-detectable.

*Use*.—Table grape.

Disease and insect resistance: This cultivar is tolerant to one of the main diseases of this species such as *Erysiphe necator*.

This cultivar is susceptible to diseases of its species, such as *Plasmopara viticola, Botrytis cinerea, Daktulosphaira vitifoliae, Ceratitis capitata, Planococcus ficus, Planococcus citri, Empoasca vitis*.

What is claimed:

1. A new and distinct variety of grapevine plant named 'BLOMG03' as substantially described and illustrated herein.

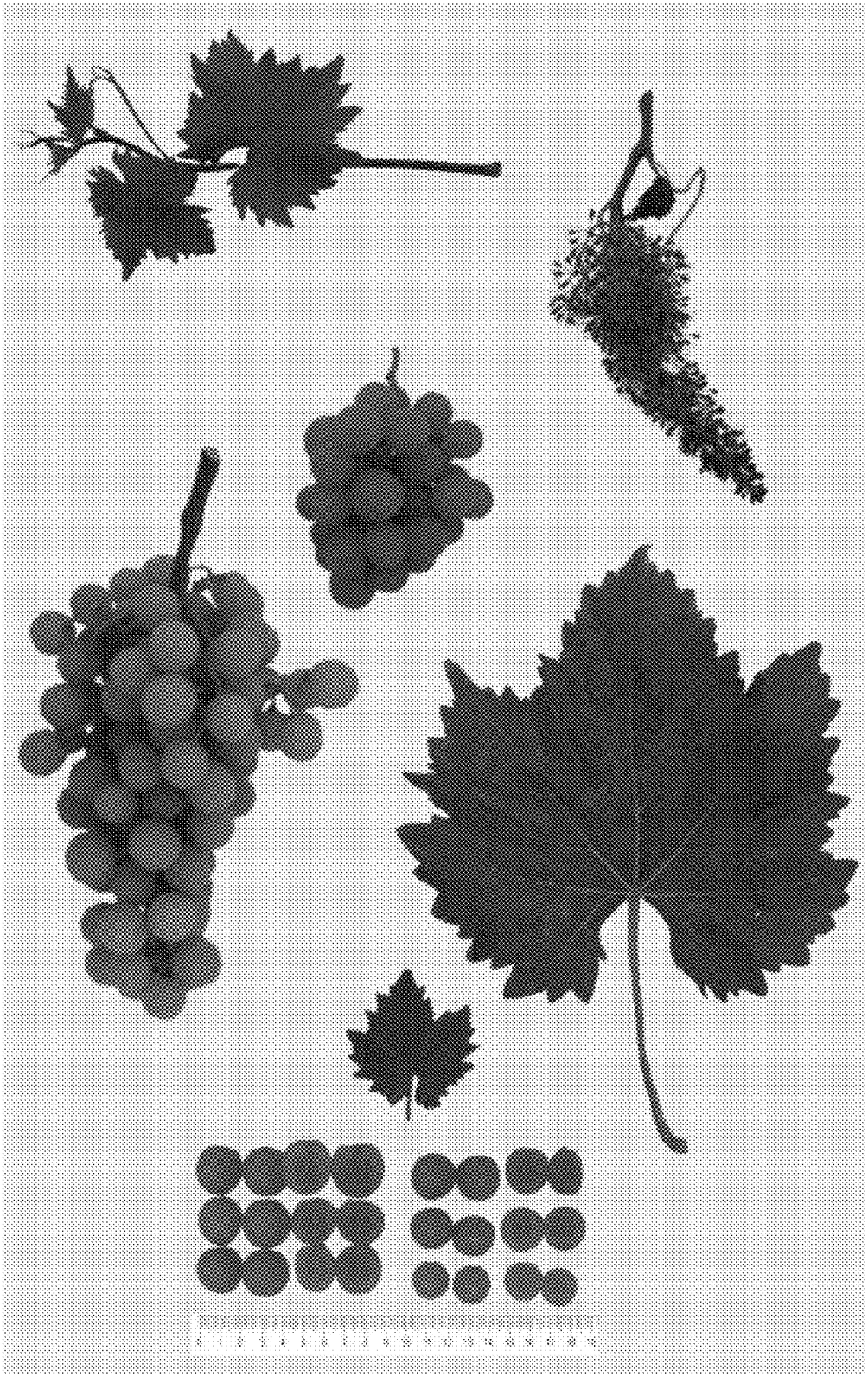

* * * * *